United States Patent [19]

Suzuki

[11] Patent Number: 5,234,666

[45] Date of Patent: * Aug. 10, 1993

[54] ALCOHOL CONTENT DETECTOR

[75] Inventor: Hiroyoshi Suzuki, Himeji, Japan

[73] Assignee: Mitsubishi Denki K.K., Tokyo, Japan

[*] Notice: The portion of the term of this patent subsequent to May 5, 2009 has been disclaimed.

[21] Appl. No.: 785,061

[22] Filed: Oct. 30, 1991

[30] Foreign Application Priority Data

Nov. 1, 1990 [JP] Japan .................................. 2-293570

[51] Int. Cl.$^5$ ............................................. G01N 21/41
[52] U.S. Cl. .................................. 422/820.9; 422/84; 436/132; 356/135
[58] Field of Search .................... 422/82.09, 83, 84; 436/131–132; 356/128–137

[56] References Cited

U.S. PATENT DOCUMENTS

| | | | |
|---|---|---|---|
| 4,853,551 | 8/1989 | Wagner et al. | 378/160 |
| 4,920,550 | 4/1990 | Olivier et al. | 378/55 |
| 5,015,091 | 5/1991 | Suzuki et al. | 356/135 |
| 5,110,205 | 5/1992 | Suzuki et al. | 356/135 |

Primary Examiner—Lyle Alexander
Attorney, Agent, or Firm—Sughrue, Mion, Zinn, Macpeak & Seas

[57] ABSTRACT

A light emitted from the light emitting element is introduced to the refraction surface formed in one part of the transparent body to cause the light beam to refract at least once and to impinge upon the first dimensional optical position detector element, thereby detecting index of refraction of fuel in accordance with the position at which the light beam impinges on the first dimension optical position detector element and bubbles in the fuel can be detected in accordance with the relative value relationship between the total light-receiving amounts. Alternatively, the monitor for monitoring the light emission from the light emitting element may be provided, and detecting bubbles in the fuel in accordance with the relative value relationship between the total light-receiving amount and an output from the monitor. Further, the light-emitting element may be controlled by the light-emitting element control so that the output from the total light-receiving amount detector is maintained constant.

19 Claims, 8 Drawing Sheets

ALCOHOL CONTENT DETECTOR

BACKGROUND OF THE INVENTION

This invention relates to an alcohol content detector device for determining the nature of the fuel supplied to a burner or the like in a non-contact manner and, more particularly, to an alcohol content detector device for measuring alcohol content of the alcohol-containing fuel used in an engine for automobiles or the like.

Recently, the U.S.A. and various European countries have adopted, as an automobile fuel, a mixed fuel containing alcohol in gasoline for the purpose of reducing consumption of petroleum, and such fuel is being diffused gradually among consumers. However, when such alcohol-mixed fuel is used, as its is, in those combustion engines originally matched with the air-fuel ratio of the fuel gasoline, there occurs a leaning phenomenon due to the fact that alcohol has a smaller theoretical air-fuel ratio than that of gasoline, and other facts. On account of this, it becomes necessary to regulate the air-fuel ratio, the ignition timing of the engine, and so forth in accordance with the alcoholic content in the fuel by controlling an actuator such as fuel injection valve, etc. through detection of the alcoholic content in the alcohol-mixed fuel. The description of such conventional alcoholic content detector device will now be made in conjunction with the drawings.

FIG. 6 is a schematic diagram illustrating an engine control system having incorporated therein a conventional alcoholic content detector device. In the Figure, A designates an alcohol content detector, (20) is an engine, (21) is a fuel tank, (22) is a fuel pump disposed within the fuel tank (21), (23) is a fuel supply pipe connected to the fuel pump (22), (24) is a high pressure filter inserted in the fuel supply pipe (23), (25) is a fuel distributor connected to the fuel supply pipe (23), (26) is a fuel pressure regulator connected to the fuel distributor (26), (27), is a fuel injection valve connected to the fuel distributor (25), (28) is a fuel return pipe connected to the fuel pressure regulator (26), (29) is an intake pressure sensor connected to an air intake pipe (30), (31) is an air-to-fuel ratio sensor mounted to an exhaust pipe (32), (33) is an engine revolution sensor, (34) is an ignition plug mounted to the engine (34), and (35) is an engine control unit, to which various signals such as the signal from the alcohol content detector A, the signal from the intake pressure sensor (29), the signal from the air-to-fuel ratio sensor (31) and the signal from the engine revolution sensor (33) are inputted and which controls the fuel injection valve (27) and the ignition plug (34) at control amounts in accordance with the input. In the figure, when fresh fuel is supplied to the fuel tank (21), the mixed fuel mixed within the fuel tank (21) is pumped through the fuel supply pipe (23) and the high pressure filter (24) by the fuel pump (22) as soon as the engine (20) is started to be introduced to the alcohol content detector A, where the alcohol content is measured. The fuel then flows into the fuel distributor (25) from where one portion of the fuel is supplied to the engine (20) through the fuel injection valve (27), and the other portion of the fuel is returned to the fuel pump (21) through the fuel pressure regulator (26) and the fuel return pipe (28). The fuel then flows into the fuel distributor pipe (25) and one portion thereof is supplied to the engine (20) through the fuel injection valve (27) and the remaining portion is returned to the fuel tank (21) through the fuel pressure regulator (26) functions to maintain the fuel pressure in the pipe up to the fuel pressure regulator (26) constant irrespective of the amount of injected fuel. When the alcohol content measured in the alcohol content detector A is inputted into the engine control unit (35), the engine control unit (35) determines the engine conditions on the basis of the signals from the engine rotation sensor (33) and the air intake pressure sensor (29) to control the valve-open time of the fuel injection valve (27), thereby changing the fuel amount supplied to the engine (20), and the air-to-fuel ratio is detected by the air-to-fuel ratio sensor (31) so that it is feed-back controlled toward a target value corresponding to the above engine conditions, upon which the ignition timing of the ignition plug (34) is controlled in accordance with the engine conditions.

FIG. 7 is a schematic diagram illustrating a conventional alcohol content detector, in which (1) is a light emitting element, (2) is a diaphragm disposed in front of the light emitting element (1), (3) is a collecting lens disposed in front of the diaphragm (2), (4) is a collected light beam and (5) is a cylindrical transparent body having formed thereon a refraction surface (51) which is cut at a predetermined angle relative to its longitudinal axis and which is in contact with the fuel introduced from the fuel inlet (81), (6) is a back side reflection mirror having a reflection surface on the opposite side of the fuel-contacting surface, (7) is a first dimension position detector element, which in this example is a semiconductor position detector element (hereinafter referred to as PSD), (8) is a case having formed therein the fuel inlet (81) for introducing the fuel onto the refraction surface (51) of the cylindrical transparent body (5), (9) is a seal including a seal portion (91) which seals between the cylindrical transparent body (5) and the case (8) and a seal portion (92) which seals between the case (8) and the fuel passage, (10) is a detection circuit comprising a current-voltage converter (101) for the photocurrent from the PSD (7), an adder (102), a divider (103), an output gain setting portion (104), an output bias setting portion (105) and a driver (106) for driving the light emitting element (1).

In the figure, when the light emitting element (1) disposed at one end of the cylindrical transparent body (5) is driven by the driver (106) to emit light, the emitted light passes through the diaphragm (2) and collected by the collective lens (3). The collected light beam (4) impinges at an incident angle $\phi$ at a point Po on the fuel-contacting refraction surface (51) disposed at the other end of the cylindrical transparent body (5) to refract at the refraction surface (51) at a refraction angle X determined in accordance with the difference between the index of refraction Nf of the fuel and the index of refraction Nd of the cylindrical transparent body (5)

$$X = \arcsin(Nd/Nf \times \sin\phi).$$

The refracted light passes through the fuel and reflected at the reflection surface P1 on the back side reflection mirror (6) to again pass through the fuel and impinges again at a point P2 on the refraction surface (51), where the light refracts in accordance with the above equation between the incident angle $\phi$ and the refraction angle X to pass into the cylindrical transparent body (5) and reach the PSD (7) disposed on the same side of the light emitting element (1). The collection lens (3) is adjusted so that the collected light beam (4) is focused substantially on the PSD (7). When the collected light beam (4) impinges on the PSD (7), photo-currents ir1 and ir2 corresponding to the incoming light amount flow from the PSD (7) to each of electrodes I1 and I2, the photo-currents ir1 and ir2 being divided in inverse proportion to the distance to the electrodes. That is, the distance X from the electrode I2 of the PSD (7) to the light impinging position is expressed by $$X = L \times ir1 / (ir1 + ri2)$$

where L is the distance between the electrodes. At this time, the distance X coincides with the center of gravity of the spot of the impinged light beam. Each of the photo-currents ir1 and ir2 is inputted to the detector circuit (10) and current-voltage converted into Vr1 and Vr2, respectively, in the current-voltage conversion unit (101). The voltages Vr1 and Vr2 are added in the adder (102) and the divider (104) computes Vr1 / (Vr1 + Vr2) on the basis of the voltage Vr1 and the result of the above addition. The computation result is multiplied by an output voltage gain K in the output gain setting unit (103), and a predetermined voltage bias Vo is applied at the output bias setting unit (105), whereby a voltage Vout corresponding to alcohol content Cm given by the equation Vout = K × vr1 / (vr1 + Vr2) + Vo is outputted. FIG. 8 is a graph illustrating the output characteristics of the alcohol content detector in connection with a methanol-gasoline mixed fuel, from which it is seen that, when the alcohol content is 0%, i.e., pure gasoline only, the difference in refraction index between the gasoline and the cylindrical transparent body (5) is small, so that the collected light beam (4) impinges on the PSD (7) on the side close to the light emitting element (1) to establish the relationship ir1 < ir2, and when the alcohol content is 100%, i.e., pure methanol only, the difference in refraction index between the gasoline and the cylindrical transparent body (5) is large, so that the collected light beam (4) impinges on the PSD (7) on the side remote from the light emitting element (1) to establish the relationship ir > ir2, whereby the illustrated output characteristic is obtained.

When the engine (20) stops at an elevated temperature and the fuel pump (22) stops, the fuel pressure in the high pressure pipe decreases and bubbles generate within the pipe, establishing a state in which bubbles exist within the fuel at the time of re-starting the engine, and when the alcohol content detector is connected in the fuel return pipe (28) at the downstream of the fuel pressure regulator (26), the fuel containing bubbles generated by the cavitation phenomenon at the fuel pressure regulator (26) passes through the alcohol content detector. However, in the conventional alcohol content detector, the bubbles mixed within the fuel cannot be detected even when they passed through the detection unit of the detector and the output change due to the passage of the the bubbles is erroneously recognized as the change in alcohol content. FIG. 9 is a sectional view of the detection unit of the conventional alcohol content detector, which illustrates the state in which the bubbles (36) in the fuel introduced from the fuel inlet (81) are in the vicinity of the refraction surface (51) of the cylindrical transparent body (5). In this condition, since the difference in the index of refraction of the cylindrical transparent body (5) and the index of refraction of the bubbles (36) is large, the collected light beam (4) passing through the cylindrical transparent body (5) is refracted at a large angle at the refraction surface (51) and is scattered or absorbed at the casing (8) and the like, so that only a very weak scattered light or no light at all impinges at the PSD (7), causing the output Vout to exhibit an unstable value which does not depend upon the alcohol content. That is, in the conventional alcohol content detector, the output variation due to the bubbles and the output alcohol cannot be distinguished from each other, so that change in output due to the bubbles is erroneously recognized as the output change due to the change in alcohol content and the engine fuel amount, the ignition timing and the like are controlled. Therefore, there was a fear that a mulfunction of the engine such as non-smooth starting of the engine and an abrupt engine stall may occur depending upon the conditions of the bubbles.

SUMMARY OF THE INVENTION

The present invention has been made in order to solve the above problems and has as its object to provide an alcohol content detector capable of detecting bubbles within the fuel without erroneously recognizing the change in the alcohol content.

The device for detecting alcoholic content of the first invention of the present application comprises a light emitting element disposed on one side of a light transparent body, a first dimension optical position detector element disposed on the same or opposite side of the transparent body, an alcohol content detector having formed in one part of the transparent body a refraction surface with respect to fuel, with light introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, and a bubble detector for detecting bubbles in the fuel in accordance with the relative value relationship between the total light-receiving amounts.

The device for detecting alcoholic content of the second invention of the present application comprises a light emitting element disposed one side of a light transparent body, a first dimension optical position detector element disposed on the same or opposite side of the transparent body, an alcohol content detector having formed in one part of the transparent body a refraction surface with respect to fuel, light is introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, a monitor unit for monitoring emission of light of the light-emitting element, and a bubble detector for detecting bubbles in the fuel in accordance with the relative value relationship between the total light-receiving amount and an output from the monitor.

The device for detecting alcoholic content of the third invention of the present invention comprises a light emitting element disposed one side of a light transparent body, a first dimension optical position detector element disposed on the same or opposite side of the transparent body, an alcohol content detector having formed in one part of the transparent body a refraction surface with respect to fuel, light being introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, a light-emitting element control unit for controlling the light-emitting element so that an output from the total light-receiving amount detector unit is maintained constant, and bubble detector means for detecting bubbles in the fuel in accordance with the relative value relationship between output signals from the light-emitting element control unit.

In the first invention of the present application, the light emitted from the light emitting element is introduced to the refraction surface formed in one part of the transparent body to cause the light beam to refract at least once and to impinge upon the first dimensional optical position detector element, thereby detecting index of refraction of fuel in accordance with the position at which the light beam impinges on the first dimension optical position detector element and detecting bubbles in the fuel in accordance with the relative value relationship between the total light-receiving amounts. In accordance with the second invention of the present application, the index of refraction of the fuel is detected in accordance with the position at which the light impinges on the first dimension optical position detector element, and the monitor for monitoring the light emission from the light emitting element is provided, and detecting bubbles in the fuel in accordance with the relative value relationship between the total light-receiving amount and an output from the monitor means. In the third invention of the present application, the index of refraction of the fuel is detected in accordance with the position at which the light impinges on the first dimension optical position detector element, and the light-emitting element is controlled by the light-emitting element control means so that the output from the total light-receiving amount detector means is maintained constant, and the bubbles in the fuel is detected in accordance with the relative value relationship between output signals form the light-emitting element control means.

BRIEF DESCRIPTION OF THE DRAWINGS

The present invention will become more readily apparent from the following detailed description of the preferred embodiments of the present invention taken in conjunction with the accompanying drawings, in which.

DESCRIPTION OF THE PREFERRED EMBODIMENTS

Figure 1:
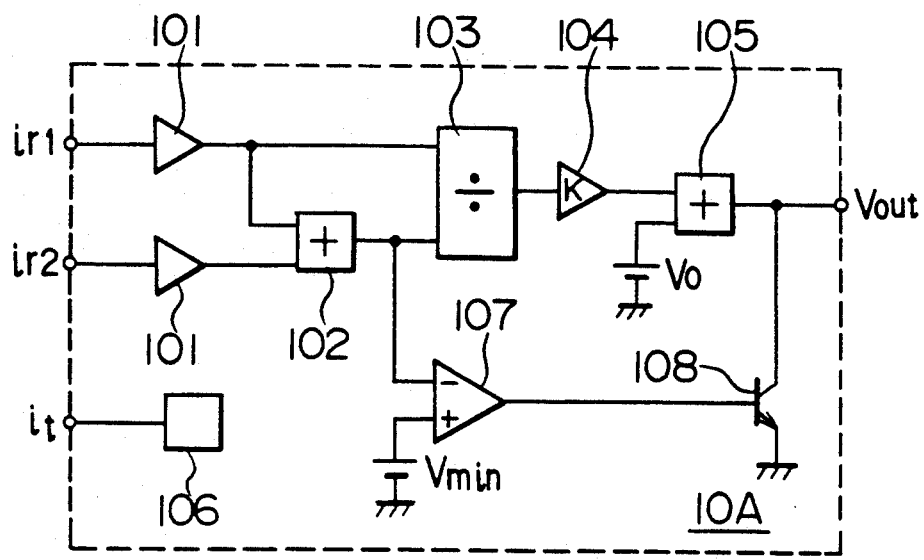
FIG. 1 is a schematic diagram illustrating one embodiment of the present invention.

One embodiment of the present invention will now be described in conjunction with the drawings. FIG. 1 is a schematic diagram illustrating one embodiment of the present invention, in which (101)~(106) are components similar to those previously described. Also, the detection unit (1)~(9) are not illustrated because they are identical to those of the conventional device. (107) is a comparator of which an inverse input terminal is connected to an output of the adder (102) and a non-inverse input terminal is connected to a d.c. power source having a voltage value of Vmin, (108) is an output controlled transistor having a base connected to an output of the comparator (107), a collector connected to an output of the output bias setting unit (105) and an emitter connected to the earth.

Figure 2:
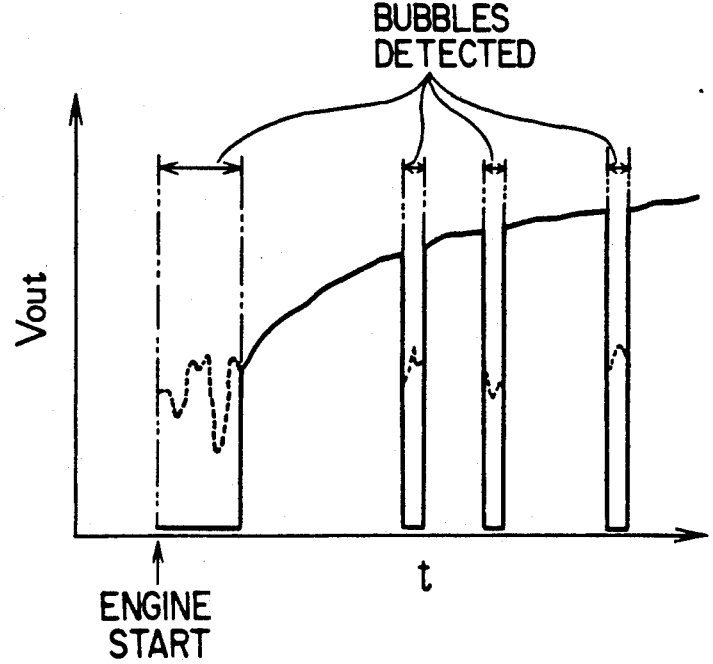
FIG. 2 is an explanatory view illustrating the output from the detection circuit of the present invention in comparison with that of the conventional device.
Figure 7:
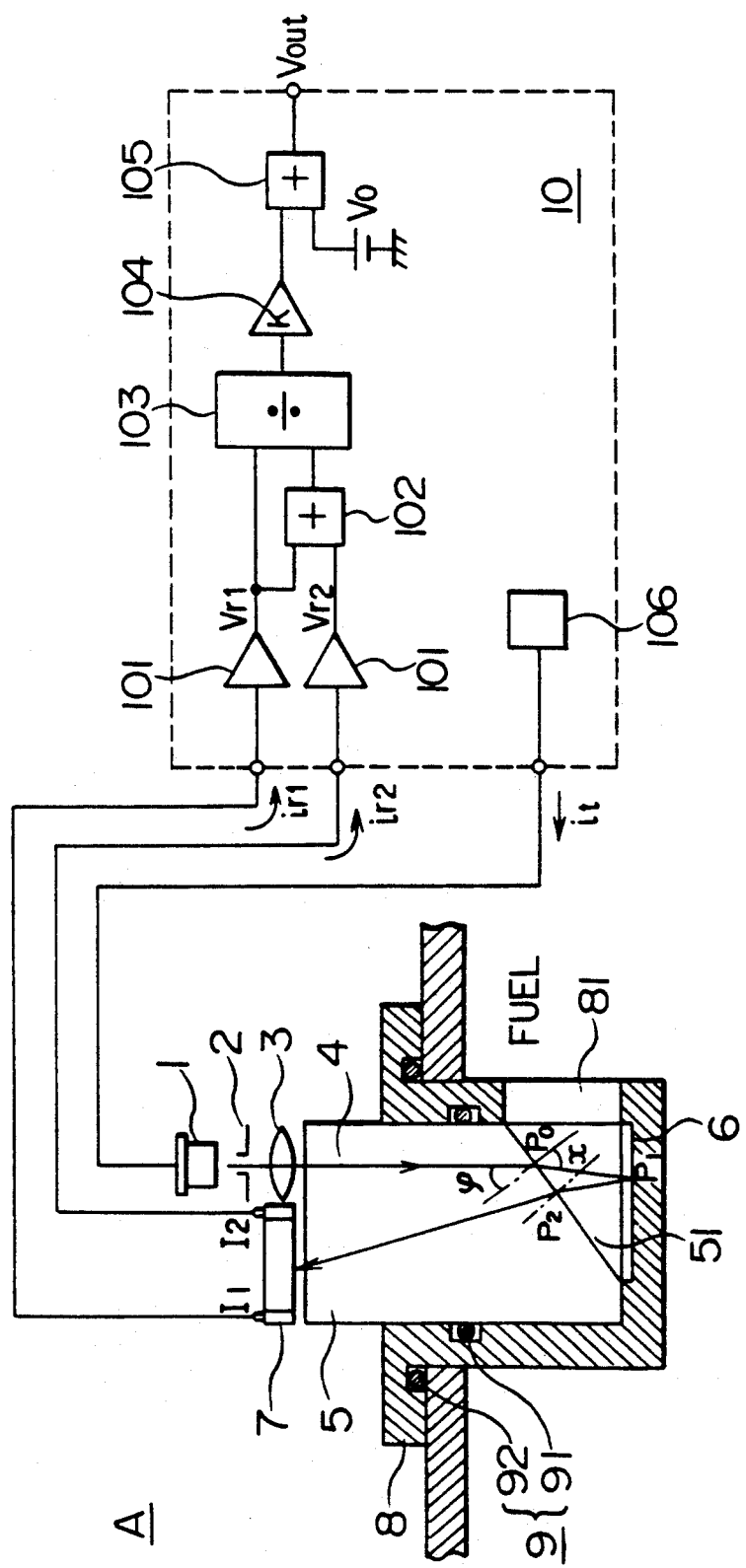
FIG. 7 is a schematic diagram illustrating a conventional alcohol content detector.
Figure 8:
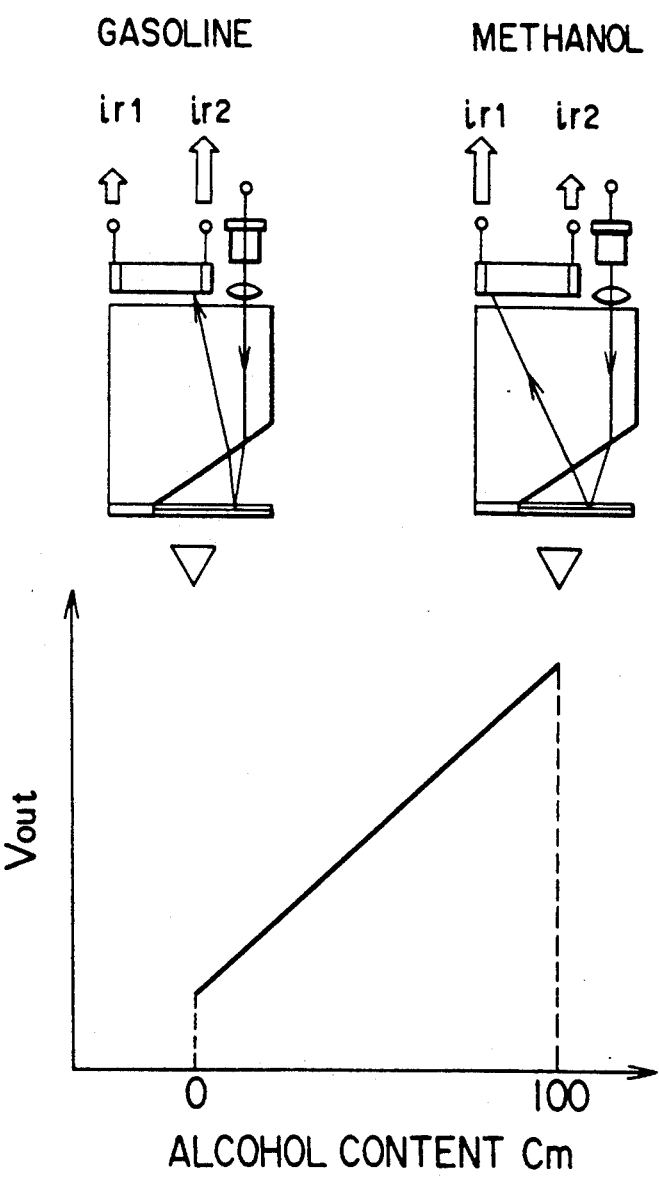
FIG. 8 is an output characteristic diagram of the conventional alcohol content detector.
Figure 9:
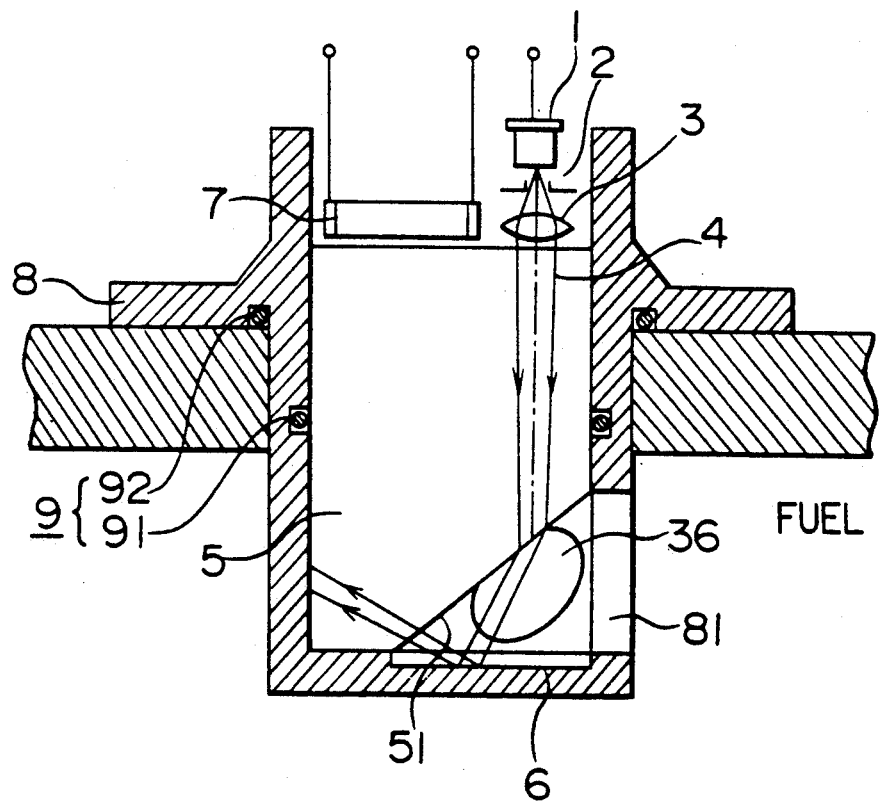
FIG. 9 is a sectional view of a known detector unit.

The operation of one embodiment of the present invention illustrated in FIG. 1 will now be made by referring to FIGS. 7 and 9 used for explaining the conventional device. In FIG. 7, when the light emitting element (1) is driven by the driving unit (106) to emit light, the emitted light is passed through the diaphragm (2) and collected by the collection lens (3). The collected light beam (4) impinges at the refraction surface (51) contacting with the fuel at the other end of the cylindrical transparent body (5) at the point Po at an incident angle $\phi$ to refract at the refraction surface (51) at a refraction angle X determined in accordance with the difference between the index of refraction Nf of the fuel and the index of refraction Nd of the cylindrical transparent body (5). The refracted light passes through the fuel and reflected at the reflection surface P1 on the back side reflection mirror (6) to again pass through the fuel and impinges on the refraction surface (51) at the point P2, where the light refracts to enter into the cylindrical transparent body (5) and is focused on he PSD (7) disposed on the same side of the light emitting element (1). Then, the signal light becomes the divided photo-currents ir1 and ir2 divided in correspondence with the position of incidence X and outputted from the electrodes I1 and I2. The photo-currents ir1 and ir2 are inputted to the detector circuit (10A) and current-voltage converted into Vr1 and Vr2, respectively, in the current-voltage conversion unit (101). The voltages Vr1 and Vr2 are added in the adder (102) and the divider (104) computes Vr1 / (Vr1+Vr2) on the basis of the voltage Vr1 and the result of the above addition. The computation result is multiplied by an output voltage gain K in the output gain setting unit (103), and a predetermined voltage bias Vo is applied at the output bias setting unit (105), whereby a voltage Vout corresponding to alcohol content Cm is outputted. At this time, when the bubble (36) in the fuel introduced from the fuel inlet (81) stays in the vicinity of the refraction surface (51) of the cylindrical transparent body (5) as illustrated in FIG. 9, the collected light beam (4) passing through the cylindrical transparent body (5) is refracted at the refraction surface (51) at a large angle and is scattered or absorbed at the casing (5) and the like, so that only a very weak scattered light or no light at all impinges at the PSD (7), causing the divided currents ir1 and ir2 to have only a very small dark current component due to temperature and the photo-current component generated by the weak scattered light, resulting in very small current as compared to the currents in the ordinary conditions in which the detection unit is filled with the fuel. The divided currents ir1 and ir2 when such bubble (36) stays are current-voltage converted into Vr1 and Vr2, respectively, in the current-voltage conversion unit (101) and then added by the adder (102), and the result of the above addition, i.e., the total photo-current value (Vr1+Vr2) is compared with a predetermined voltage value Vmin at the comparator (107). When (Vr1+Vr2)≦Vmin, the output control transistor (108) is turned on to decrease the output Vout to LOW thereby detecting the bubble. On the other hand, when the detection unit is filled with the fuel, the total photo-current value (Vr1+Vr2) is sufficiently larger than the voltage value Vmin, so that the signal from the output bias setting unit (105) is directly outputted as the output Vout. FIG. 2 is a graph illustrating the output Vout of the alcohol content detector of the above embodiment when the engine (20) is started with the bubbles contained in the fuel system as compared to that of the conventional device, from which it is understood that, while the the output variation due to the bubbles cannot be distinguished from that due to the variation in the alcohol content in the convention device, the bubble detection can be achieved by the LOW state of the output Vout in this embodiment, so that there is no fear of erroneously recognizing the output variation due to the bubbles as the variation in the alcohol content.

Figure 3:
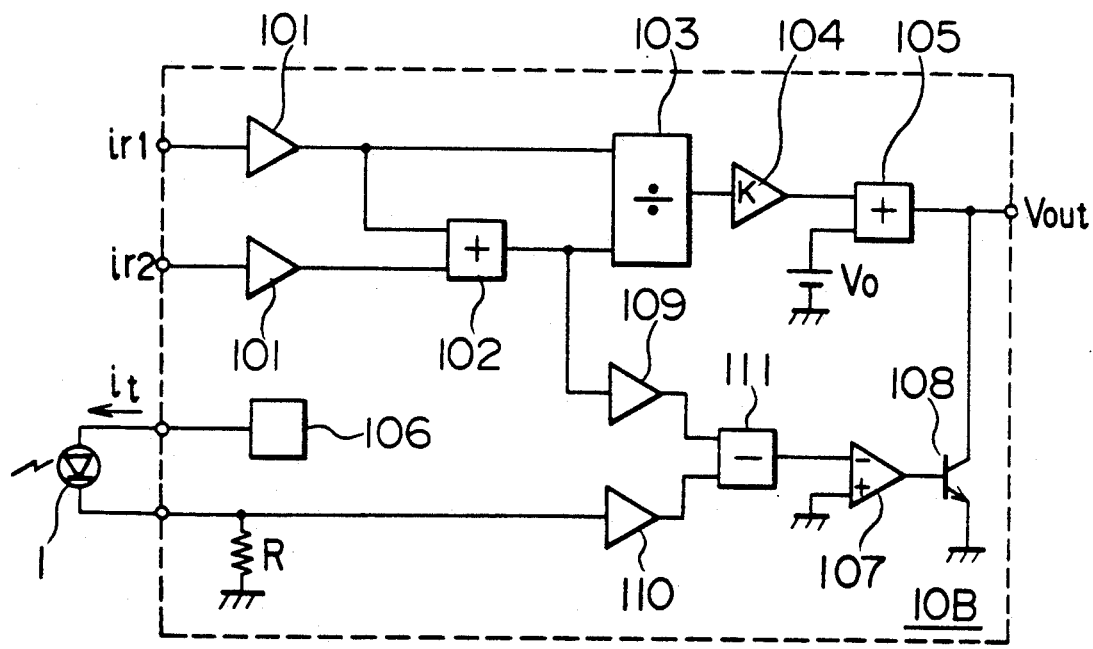
FIGS. 3~5 are schematic diagrams illustrating various embodiments of the present invention.

FIG. 3 is a schematic diagram illustrating another embodiment of the present invention, the description will be made with the same reference numerals assigned to the corresponding components shown in FIG. 1. The detection circuit (10B) of this embodiment comprises a total received light amount gain setting unit (109), a light emission current detection unit (110) and a subtractor unit (111) all connected to the inputs of the comparator (107). One of the inputs of the subtractor unit (111) is connected to the output of the adder unit (102) through the total received light amount gain setting unit (109), the other input of the subtractor unit (111) is connected to the light emitting element (1) through the light emission current detection unit (110), and the output of the subtractor (111) is connected to the inverse input terminal of the comparator (107). Also, a resistor R is connected between the input of the light emission current detector unit (119) and the ground.

The operation of this embodiment of the present invention illustrated in FIG. 3 will now be described. From the output of the total received light amount gain setting unit (109) which is the total photo-current (Vr1+Vr2) multiplied by a predetermined gain K, a current it if the light emitting element (1) detected by the resistor R at the light emission current detector unit (110) is subtracted. The subtracted result [K(Vr1+Vr2)−it] is compared by the comparator (107), and when the subtraction result is smaller than zero, it is assumed that the bubble is detected and the output control transistor (108) is turned on to decrease the output Vout LOW in a manner similar to that in the previous embodiment. That is, in this embodiment, bubbles in the fuel are detected on the basis of the magnitude relationship with respect to the light emission current of the light emitting element (1), whereby it is advantageously distinguished from the condition in which the normal light emission is not achieved because of the mulfunction of the light emitting element (1) or the like. Although the process of the above distinction is not illustrated in the figure, the mulfunction of the light emitting element (1) or the like can be determined when the light emission current is zero even when the output Vout is not in the LOW state by externally taking out the signal from the light emission current detection unit (111).

Figure 4:
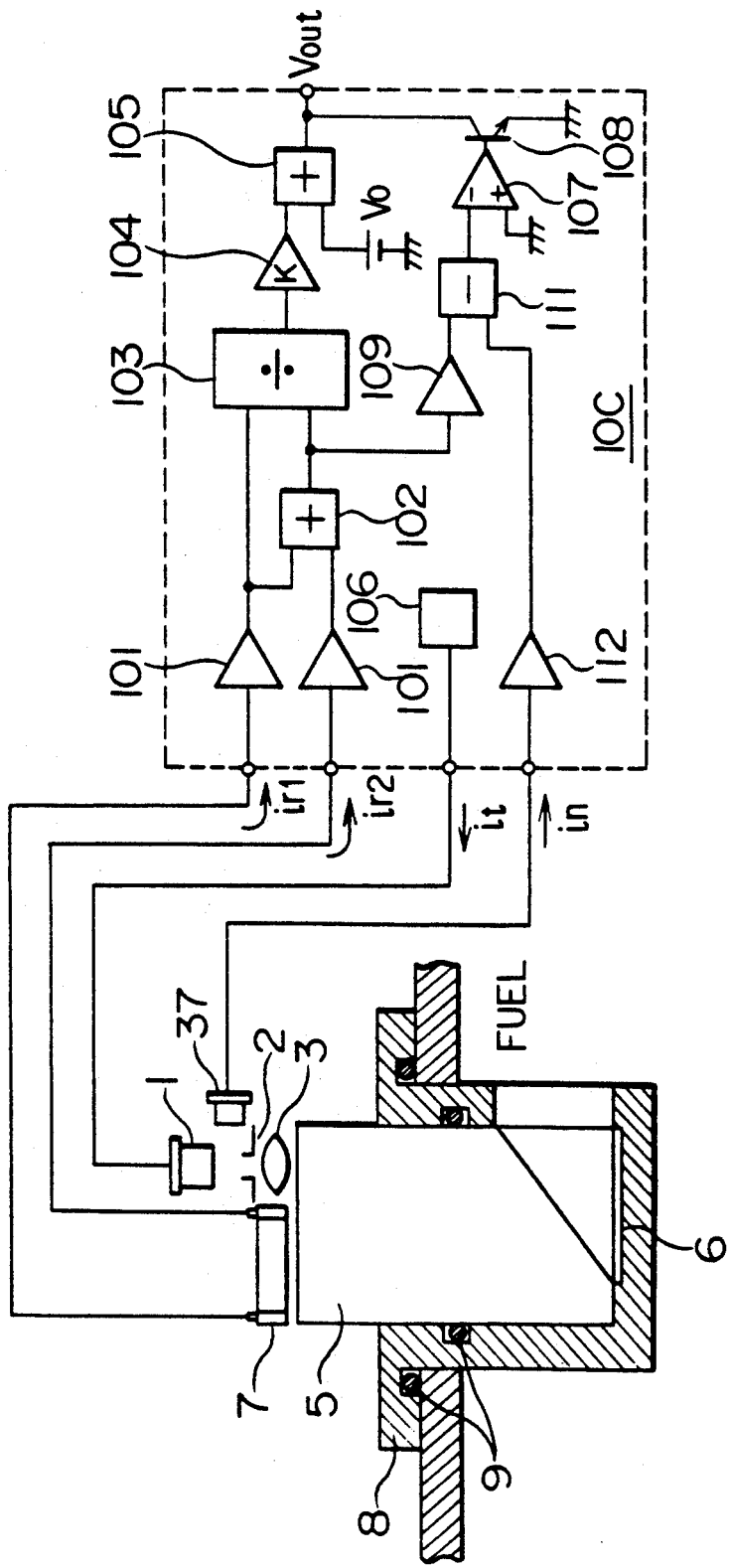

FIG. 4 is a schematic diagram illustrating another embodiment of the present invention. In this embodiment, a monitor light receiving element (37) is provided in the vicinity of the light emitting element (1) for monitoring the light emitting state of the light emitting element (1) and for supplying the output from the monitor light receiving element (37) to the other input of the subtraction unit (111) through the monitor light receiving amount detector unit (112) of the detection circuit (10C). That is, the light receiving amount im of the monitor light receiving element (37) is detected by the monitor light receiving amount detector unit (112), and this value is subtracted in the subtraction unit (111) from a total light receiving amount of the PSD (7) multiplied by a predetermined gain k' by the total light receiving amount gain setting unit (109), and the subtraction result [k'(Vr1+Vr2)−im] is compared in the comparator (107). When the subtraction result is smaller than zero, it is assumed that the bubble is detected and the output control transistor (108) is turned on to decrease the output Vout to LOW in a similar manner to that in the previous embodiments. Therefore, in this embodiment also, similar advantageous effect as previously described can be obtained and, more over, since the light emission amount of the light emitting element (1) can be directly monitored in this embodiment, another advantage that a fault in the light emitting element (1) due to a degraded light emission efficiency or the like can be compensated for.

Figure 5:
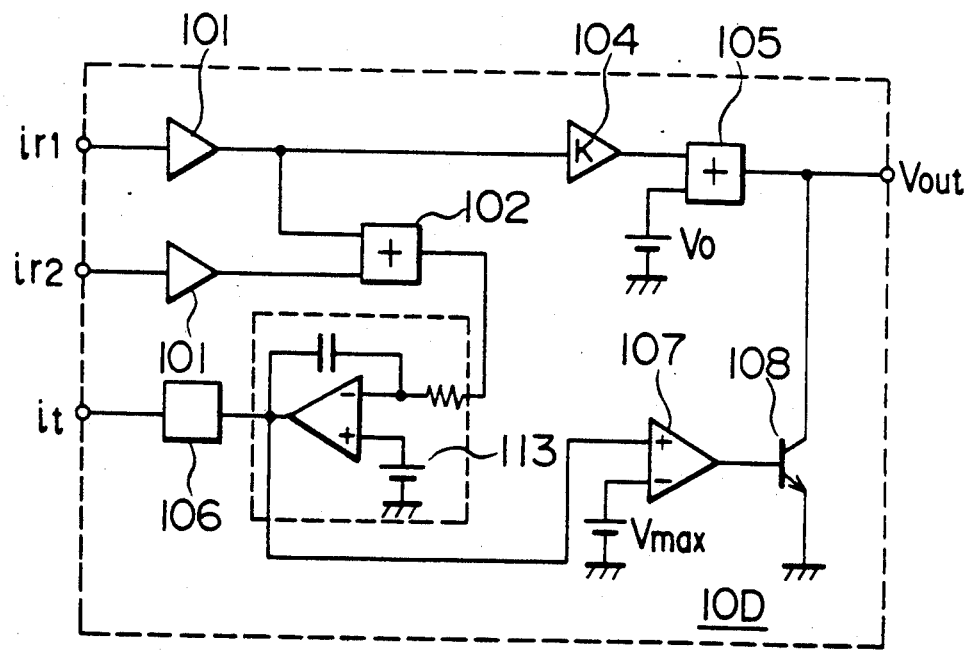
Figure 6:
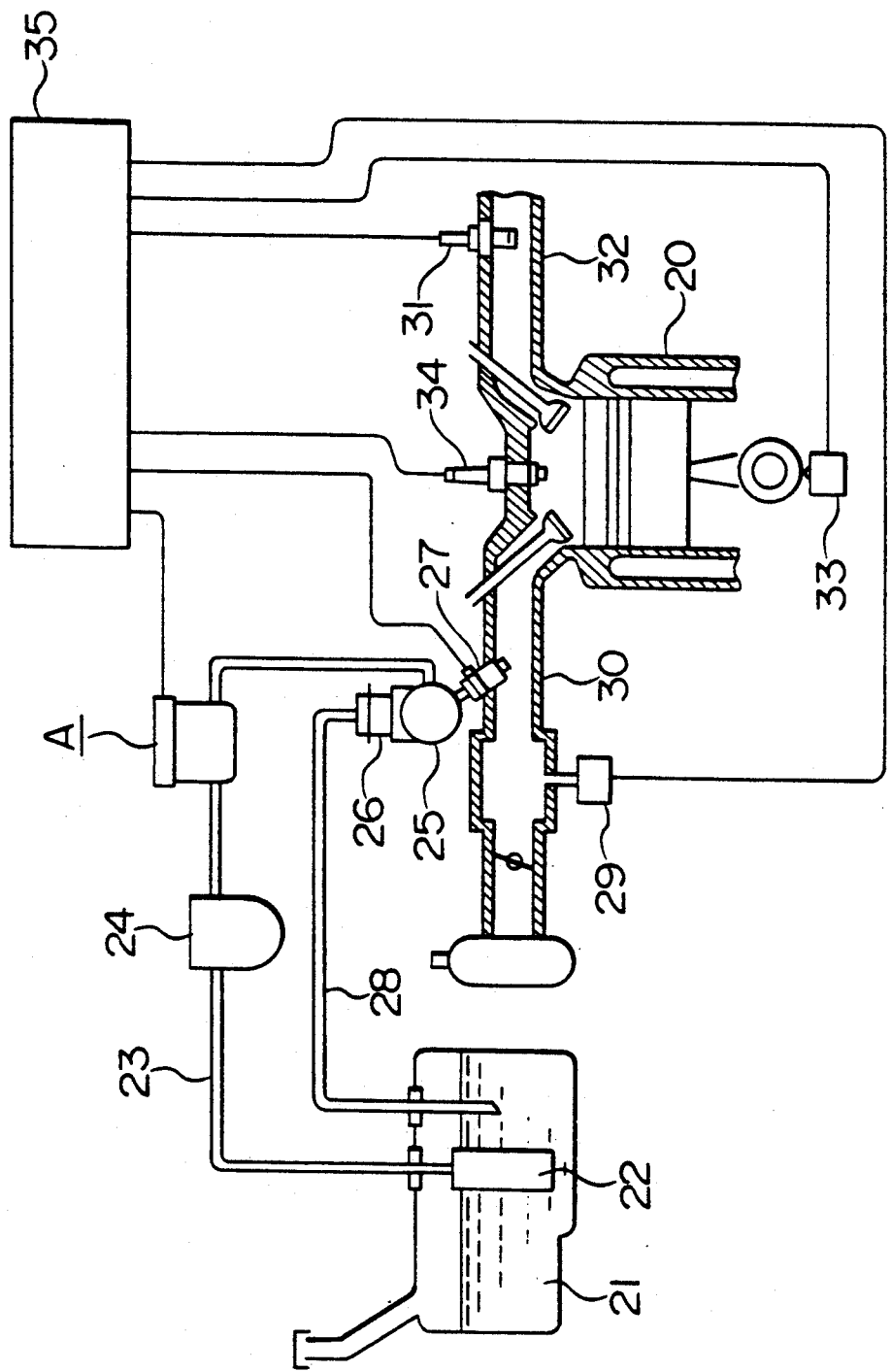
FIG. 6 is a schematic diagram illustrating a known engine control system.

FIG. 5 is a schematic diagram illustrating still another embodiment of the present invention. In this embodiment, a detection circuit (10D) comprises a light emitting element control unit (113) having an inverse input terminal connected to the output of the adder unit (102), a noninverse input terminal connected to a reference power source, and an output terminal connected to the driving unit (106), and to the noninverse input terminal of the comparator (107). The output of the total light receiving amount (Vr1+Vr2) of the PSD (7) is inputted to the light emitting element control unit (113), and the light emitting element control unit (113) provides an output signal to the driver unit (106) to control the light emitting amount of the light emitting element (1) so that the total light receiving amount (Vr1+Vr2) is maintained at a predetermined constant value. On the other hand, the output from the light emitting element control unit (113) is supplied to the comparator (107) where it is compared with a predetermined voltage value Vmax and, when it is greater than the voltage value Vmax, the output control transistor (108) is turned on to decrease the alcohol content output Vout to the LOW state. When the bubble (36) stays in the vicinity of the refraction surface (51) of the cylindrical transparent body (5), the total light receiving amount (Vr1+Vr2) of the PSD (7) becomes very small, so that the light emitting element control unit (113) supplies a large output to the driving unit (106) to increase the light emitting amount of the light emitting element (1) in order to maintain the above total light receiving amount (Vr1+Vr2) at the predetermined constant value. At this time, since the output from the light emitting element control unit (113) becomes larger than the predetermined voltage value Vmax, the output control transistor (108) is turned on and the output Vout is decreased to the LOW state, thereby indicating the presence of the bubbles. That is, also in this embodiment, the bubbles can be detected as in the previous embodiment.

Although the description has been made in terms of the embodiment in which a PSD is used as the first dimensional optical position detector element, similar position detector element such as PSD array, CCD, etc. Also, while the description has been made in terms of the embodiments where the device is used for detecting bubbles in the alcohol mixture fuel of an engine, the present invention can of course be used in detecting bubbles in other liquids.

As has been described, the device for detecting alcoholic content of the first invention of the present application comprises a light emitting element disposed on one side of a light transparent body, a first dimension optical position detector element disposed on the same or opposite side of the transparent body, an alcohol content detector having formed in one part of the transparent body a refraction surface with respect to fuel, with light introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, and a bubble detector for detecting bubbles in the fuel in accordance with the relative value relationship between the total light-receiving amounts. Therefore, an alcohol content detector capable of accurately detecting the alcohol content even when bubbles are contained within the fuel.

Also, the device for detecting alcoholic content of the second invention of the present application comprises a light emitting element disposed one side of a light transparent body, a first dimension optical position detector element disposed on the same or opposite side of the transparent body, an alcohol content detector having formed in one part of the transparent body a refraction surface with respect to fuel, light is introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, a monitor unit for monitoring emission of light of the light-emitting element, and a bubble detector for detecting bubbles in the fuel in accordance with the relative value relationship between the total light-receiving amount and an output form the monitor. Therefore, an alcohol content detector capable of accurately detecting the alcohol content even when bubbles are contained within the fuel and, moreover, capable of cope with fault in the light emitting element due such as to degrading of the light emitting efficiency.

The device for detecting alcoholic content of the third invention of the present invention comprises a light emitting element disposed one side of a light transparent body, a first dimension optical position detector element disposed on the same or opposite side of the transparent body, an alcohol content detector having formed in one part of the transparent body a refraction surface with respect to fuel, light being introduced into the refraction surface from the light-emitting element to cause the light beam to refract at least once and to impinge upon the first dimensional optical position detector element, for detecting index of refraction of fuel in accordance with the position at which the light impinges on the first dimension optical position detector element, a total light-receiving amount detector for detecting the total light-receiving amount of the first dimension position detector, a light-emitting element control unit for controlling the light-emitting element so that an output from the total light-receiving amount detector unit is maintained constant, and bubble detector means for detecting bubbles in the fuel in accordance with the relative value relationship between output signals form the light-emitting element control unit. Therefore, an alcohol content detector capable of accurately detecting the alcohol content even when bubbles are contained within the fuel.

What is claimed is:

1. A device for detecting an alcoholic content in a fuel supply, said device comprising:
   a light emitting element disposed on a first side of a light transparent body, said light transparent body having a refractive surface on a second side thereof, said fuel supply being in fluid contact with said refractive surface;
   a first position detector disposed on said first or second side of said transparent body, wherein light from the light emitting means passes through the transparent body and a portion of said fuel supply, said light being refracted by the refractive surface of said transparent body and said portion of fuel, said refractive light impinging on the first optical position detector;
   alcohol content detector means, connected to said first optical position detector, for detecting an index of refraction of the fuel supply correlated to a position at which the light impinges on said first optical position detector, said position varying based on an alcohol content of said fuel supply;
   total light-receiving detector means, connected to the first optical position detector, for detecting a total amount of light received by said first optical position detector; and
   bubble detector means, connected to the total light-receiving detector, for detecting bubbles in the fuel in accordance with said total amount of light received.

2. A device for detecting an alcoholic content in a fuel supply, according to claim 1, wherein said total light-receiving detector means includes first and second light detectors for detecting light and for outputting first and second voltages, respectively, based on an amount of detected light, and an adder for summing said first and second voltages.

3. A device for detecting an alcoholic content in a fuel supply, according to claim 1, wherein said bubble detector means further includes:
   a transistor, connected to the alcohol content detector means, for turning an output of the alcohol detector means on and off based a comparison between said total amount of light and a predetermined voltage representing a light reference level.

4. A device for detecting an alcoholic content in a fuel supply, according to claim 1, wherein said bubble detector means includes a comparator, connected to the total light-receiving detector means, for comparing an output of the total light-receiving detecting means with a predetermined voltage, said bubble detector means determining that bubbles exist in the fuel supply when the output of the total light-receiving detector means exceeds the predetermined voltage.

5. A device for detecting an alcoholic content in a fuel supply, according to claim 4, wherein said bubble detector means further includes:
   a transistor, connected to the alcohol content detector means and the comparator, for turning an output of the alcohol detector means on and off based on an output from the comparator.

6. A device for detecting an alcoholic content in a fuel supply, said device comprising:
   a light emitting element disposed on a first side of a light transparent body, said light transparent body having a refractive surface on a second side thereof, said fuel supply being in fluid contact with said refractive surface;
   a first optical position detector disposed on said first or second side of said transparent body, wherein light from the light emitting means passes through the transparent body and a portion of said fuel supply, said light being refracted by the refractive surface of said transparent body and said portion of fuel, said refractive light impinging on the first optical position detector;
   alcohol content detector means, connected to said first optical position detector, for detecting an index of refraction of the fuel supply correlated to a position at which the light impinges on said first optical position detector, said position varying based on an alcohol content of said fuel supply;
   total light-receiving detector means, connected to the first optical position detector, for detecting a total amount of light received by said first optical position detector;
   monitor means, connected to said light emitting element, for monitoring an amount of light emitted by said light emitting element; and
   bubble detector means, connected to the total light-receiving detector and monitor means, for detecting bubbles in the fuel in accordance with a relationship between said total amount of light received and an output from said monitor means.

7. A device for detecting an alcoholic content in a fuel supply, according to claim 6, wherein said total light-receiving detector means includes first and second light detectors for detecting light and for outputting first and second voltages, respectively, based on an amount of detected light, and an adder for summing said first and second voltages.

8. A device for detecting an alcoholic content in a fuel supply, according to claim 6, wherein said bubble detector means further includes:
   a comparator for comparing a predetermined voltage level with a difference between a first voltage, representing the total amount of light received by the light-receiving detector means, and a second voltage, representing an amount of current passing through the light emitting element, said bubble detector means determining that a bubble is in the fuel supply when said difference is below said predetermined level.

9. A device for detecting an alcoholic content in a fuel supply, according to claim 6, wherein said bubble detector means further includes:
   a gain setting unit for multiplying the total amount of light received by said total light-receiving detector means by a predetermined gain value,
   a current detector for determining an amount of current emitting by said light emitting element, and
   a subtractor, connected between said gain setting unit and said current detector, for outputting a difference between the output of the gain setting unit and the current detector, said bubble detector means determining that a bubble exists in the fuel supply based on said difference.

10. A device for detecting an alcoholic content in a fuel supply, according to claim 9, wherein said bubble detector means further includes:
    a comparator, connected to the subtractor, for comparing a predetermined level with said difference, and
    a transistor, connected to the alcohol content detector means and the comparator, for turning an output of the alcohol detector means on and off based on an output from the comparator.

11. A device for detecting an alcoholic content in a fuel supply, according to claim 6, wherein said monitor means further includes:
    a light monitoring element, provided near the light emitting element, for monitoring a state of the light emitting element, and
    a light monitor detector, connected to an output of the light monitoring element, for determining an amount of light received by the light monitoring element, such that said bubble detector means determines whether a bubble exists in the fuel supply based on a level of an output from the light monitor detector.

12. A device for detecting an alcoholic content in a fuel supply, according to claim 11, wherein said bubble detector means further includes:
    a gain setting unit for multiplying the total amount of light received by said total light-receiving detector means by a predetermined gain value, and
    a subtractor, connected between said gain setting unit and said light monitor detector, for outputting a difference between the output of the gain setting unit and the light monitor detector, said bubble detector means determining that a bubble is in the fuel supply based on said difference.

13. A device for detecting an alcoholic content in a fuel supply, according to claim 12, wherein said bubble detector means further includes:
    a comparator, connected to the subtractor, for comparing a reference level with said difference, and
    a transistor, connected to the alcohol content detector means and the comparator, for turning an output of the alcohol detector means on and off based on an output from the comparator.

14. A device for detecting an alcoholic content in a fuel supply, said device comprising:
    a light emitting element disposed on a first side of a light transparent body, said light transparent body having a refractive surface on a second side thereof, said fuel supply being in fluid contact with said refractive surface;

a first optical position detector disposed on said first or second side of said transparent body, wherein light from the light emitting means passes through the transparent body and a portion of said fuel supply, said light being refracted by the refractive surface of said transparent body and said portion of fuel, said refractive light impinging on the first optical position detector;

alcohol content detector means, connected to said first optical position detector, for detecting an index of refraction of the fuel supply supply correlated to a position at which the light impinges on said first optical position detector, said position varying based on an alcohol content of said fuel supply;

total light-receiving detector means, connected to the first optical position detector, for detecting a total amount of light received by said first optical position detector;

light-emitting element control means, connected to the light emitting element, for controlling said light-emitting element so that an output from said total light-receiving detector means is maintained constant; and bubble detector means, connected to the total light-receiving detector, for detecting bubbles in the fuel in accordance with a relationship between output signals from said light-emitting element control means.

15. A device for detecting an alcoholic content in a fuel supply, according to claim 14, wherein said total light-receiving detector means includes first and second light detectors for detecting light and for outputting first and second voltages, respectively, based on an amount of detected light, and an adder for summing said first and second voltages.

16. A device for detecting an alcoholic content in a fuel supply, according to claim 14, wherein said bubble detector means further includes:

a comparator for comparing an output of the light-emitting element control means with a predetermined value, said bubble detector means determining that a bubble exists in the fuel supply based on the output of the comparator.

17. A device for detecting an alcoholic content in a fuel supply, according to claim 14, wherein said light-emitting element control means includes:

an operational amplifier, connected to the total light-receiving detector means and a reference power, for controlling a light emitting amount of the light emitting element, such that the total light received by the total light-receiving detector means maintains a predetermined constant value.

18. A device for detecting an alcoholic content in a fuel supply, according to claim 17, wherein said bubble detector means further includes:

a comparator, connected to the operational amplifier, for comparing an output of the operational amplifier with a reference value, said bubble detector means determining that a bubble exists in the fuel supply when an output of the operational amplifier exceeds the reference value.

19. A device for detecting an alcoholic content in a fuel supply, according to claim 18, wherein said bubble detector means further includes:

a transistor, connected to the alcohol content detector means and the comparator, for turning an output of the alcohol detector means on and off based on a relation between the reference value and a level of the comparator output.

* * * * *